United States Patent [19]

van Andel

[11] Patent Number: Plant 5,509

[45] Date of Patent: Jul. 9, 1985

[54] ALSTROEMERIA NAMED STALPATRI

[75] Inventor: Jacob van Andel, Aalsmeer, Netherlands

[73] Assignees: B. V. Handelskwekerij; M. C. van Staaveren, Aalsmeer, Netherlands

[21] Appl. No.: 521,887

[22] Filed: Aug. 10, 1983

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Chas. W. Rummler

[57] ABSTRACT

A new and distinct alstroemeria variety particularly characterized by its medium sized, very light pink and yellow flower petals, the outer row of petals being of a uniform empire rose color and the inner petals having an indian yellow longitudinally-extending coloration for almost the entire length of the petal and the yellow areas having ruby red pencil stripes which give the flower a very distinctive appearance.

1 Drawing Figure

BACKGROUND OF THE NEW PLANT

This new alstroemeria cultivar originated as a sport of "Pink Triumph" (U.S. Plant Pat. No. 4,600) and is generally similar in its physical aspects and growth habit. This plant was discovered by me at Aalsmeer, Holland, in 1979 among a group of the parent variety and because of its very noticeable differences from its parent, I propagated this sport by means of roots of the main flowering stem at Aalsmeer for test and observation. Subsequently, I produced successive generations of this discovery plant by division of its own root stock and I have found that the successive generations of this variety have retained the novel characteristics of the discovery plant, including its novel flower color, and I have found that this novelty holds true from generation to generation and appears to be firmly fixed.

DESCRIPTION OF THE DRAWING

My new alstroemeria cultivar is illustrated by the accompanying full color photographic drawing which shows its distinguishing color characteristics as nearly true as can reasonably be obtained by conventional professional photographic procedures.

DESCRIPTION OF THE NEW PLANT

The following is a detailed description of my new alstroemeria discovery with color designations according to The R.H.S. Colour Chart of The Royal Horticultural Society of London, England.

THE PLANT

Origin: Sport.
Parentage: Pink Triumph (U.S. Plant Pat. No. 4,600).
Classification: Alstroemeria.
Form: Bush. A tall, slender and rigid stalk with flower bearing branches at its top in simple umbel form.
Height: About 1.70 meters.
Growth: Vigorous, upright and strong.
Root Stock: Tuberous.
Foliage:
- *Quantity.*—Abundant.
- *Number of leaves.*—About 30 to 40 per stem.
- *Size of leaf.*—Depends on season.
- *Shape of leaf.*—Elliptic.
- *Texture.*—Leathery.

- *Color.*—Upper side — Dark Green. Under side — Grey Green.

THE BUD

Form: Pear-shaped.
Size: Medium.
- *Diameter.*—About 15 mm.
- *Length.*—About 40 to 45 mm.

Opening: Slowly. This bud has no calyx and the six petals of the flower are a perianth.
Peduncle:
- *Length.*—About 2 cm.
- *Character.*—The peduncle is sturdy and extends at an angle of about 30° with the umbel stem.

THE FLOWER

Blooming habit: Continuous and profuse during early Spring and Fall blooming seasons.
Flower size: Medium.
- *Diameter.*—About 6 cm.
- *Depth.*—About 5 cm.

Borne: Singly on a relatively long umbel stem.
Shape: Funnel-like.
Petalage:
- *Number of petals.*—Six arranged in two concentric rows of three.
- *Form.*—Broad ovate.
- *Texture.*—Soft.
- *Appearance.*—Shiny.
- *Color.*—The principal color of all petals is empire rose 48C except for the indian yellow 17B and ruby red 59A streaked portions of the inner petals and any variation of the main petal color of 48C, as shown, is entirely due to camera position and lighting of the subject.

Persistence: The flowers hang on and dry.
Lasting quality:
- *On the plant.*—15 to 20 days.
- *As a cut flower.*—10 to 15 days.

REPRODUCTIVE ORGANS

Stamens:
- *Number.*—Six arranged one opposite each petal.
- *Anthers.*—Size: About 8 to 10 mm. Color: Yellow Green.
- *Filaments.*—Length: About 4 cm. Color: Pink.
- *Pollen.*—Color: Yellow.

Pistils:

*Number.*—One.

*Style.*—Length: About 5 mm. Color: Pink.

*Stigma.*—Color: Pink.

This sport retains most of the physical and growth characteristics of its parent Pink Triumph, the primary difference being the flower coloration which makes the new plant an attractive addition to the alstroemeria field.

I claim:

1. A new and distinctive alstroemeria variety, substantially as herein shown and described, characterized by the distinctive empire rose-and indian yellow coloration of its medium sized and profusely blooming flowers.

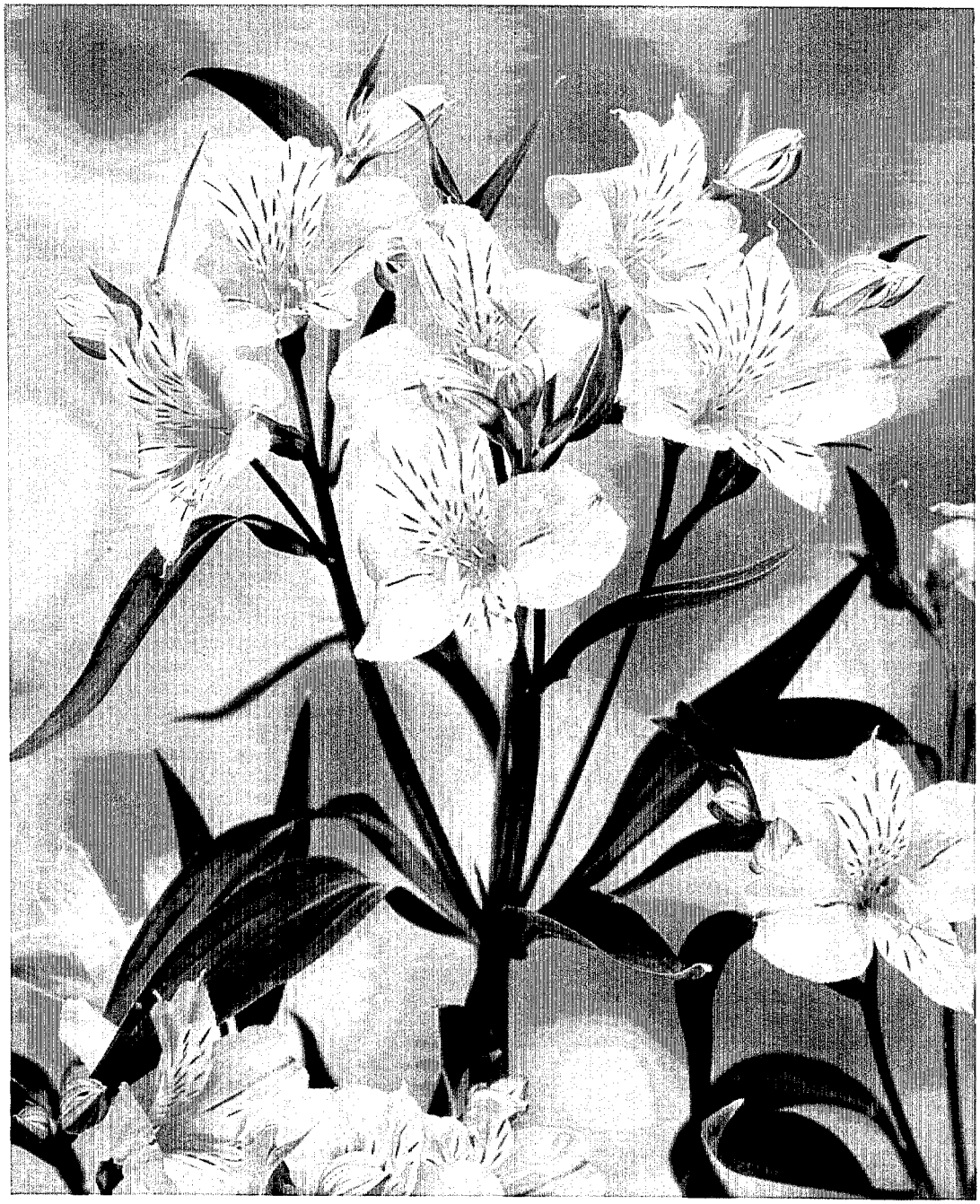

* * * * *